United States Patent
Braig et al.

(10) Patent No.: US 6,636,753 B1
(45) Date of Patent: *Oct. 21, 2003

(54) SOLID-STATE NON-INVASIVE INFRARED ABSORPTION SPECTROMETER FOR THE GENERATION AND CAPTURE OF THERMAL GRADIENT SPECTRA FORM LIVING TISSUE

(75) Inventors: James R. Braig, Alameda, CA (US); Bernhard B. Sterling, Danville, CA (US); Daniel S. Goldberger, Boulder, CO (US); Joan C. Godfrey, Fremont, CA (US); Julian Cortella, Alameda, CA (US); David J. Correia, Fremont, CA (US); Arthur M. Shulenberger, Brisbane, CA (US); Charles E. Kramer, Poway, CA (US)

(73) Assignee: OptiScan Biomedical Corporation, Alameda, CA (US)

( * ) Notice: Subject to any disclaimer, the term of this patent is extended or adjusted under 35 U.S.C. 154(b) by 221 days.

This patent is subject to a terminal disclaimer.

(21) Appl. No.: 09/760,423

(22) Filed: Jan. 11, 2001

Related U.S. Application Data

(63) Continuation of application No. 09/265,195, filed on Mar. 10, 1999, now Pat. No. 6,198,949.

(51) Int. Cl.[7] .............................. A61B 5/00; G01N 21/71
(52) U.S. Cl. ................ 600/310; 250/339.03; 250/341.6
(58) Field of Search ................................. 600/310, 316, 600/322, 473; 250/341.1, 341.6, 341.5, 341.8, 339.07, 339.03, 339.06, 339.12, 339.11, 339.09, 340, 495.1; 219/553; 392/407, 416, 483

(56) References Cited

U.S. PATENT DOCUMENTS

| | | | |
|---|---|---|---|
| 3,958,560 A | 5/1976 | March | |
| 4,655,225 A | 4/1987 | Dahne et al. | |
| 5,009,230 A | 4/1991 | Hutchinson | |
| 5,137,023 A | 8/1992 | Mendelson et al. | |
| 5,191,215 A * | 3/1993 | McClelland et al. | 250/341.6 |
| 5,313,941 A | 5/1994 | Braig et al. | |
| 6,198,949 B1 * | 3/2001 | Braig et al. | 600/310 |

FOREIGN PATENT DOCUMENTS

| | | |
|---|---|---|
| CH | 612271 | 7/1979 |
| DE | WO 96/01075 | 1/1996 |

* cited by examiner

*Primary Examiner*—Eric F. Winakur
(74) *Attorney, Agent, or Firm*—Knobbe, Martens, Olson & Bear, LLP.

(57) ABSTRACT

A solid-state spectrometer for the non-invasive generation and capture of thermal gradient spectra from human or animal tissue. The spectrometer includes an infrared transmissive thermal mass window for inducing a transient temperature gradient in the tissue by means of conductive heat transfer with the tissue, and cooling means in operative combination with the thermal mass window for cooling the thermal mass window. Also provided is an infrared sensor means for detecting infrared emissions emanating from the tissue as the transient temperature gradient progresses into the tissue, and for providing output signals proportional to the detected infrared emissions. Data capture means is provided for sampling the output signals received from the infrared sensor means as the transient temperature gradient progresses into the tissue.

15 Claims, 8 Drawing Sheets

SOLID-STATE NON-INVASIVE INFRARED ABSORPTION SPECTROMETER FOR THE GENERATION AND CAPTURE OF THERMAL GRADIENT SPECTRA FORM LIVING TISSUE

CROSS-REFERENCE TO RELATED APPLICATIONS

This application is a continuation of application Ser. No. 09/265,195 filed on Mar. 10, 1999, now U.S. Pat. No. 6,198,949.

TECHNICAL FIELD

The present invention relates to a method and apparatus for inducing a transient thermal gradient in human or animal tissue, and for obtaining thermal gradient spectra from the tissue as the thermal gradient propagates through the tissue. The resulting thermal gradient spectra can then be converted to conventional infrared spectra, which in turn can be used to determine concentrations of substances present in the tissue, such as glucose.

BACKGROUND OF THE INVENTION

Millions of diabetics are forced to draw blood daily to determine their blood sugar levels. To alleviate the constant discomfort of these individuals, substantial effort has been expanded in the search for a non-invasive methodology to accurately determine blood glucose levels. Two patent applications, each assigned to Optiscan Biomedical Corporation of Alameda, Calif., have significantly advanced the state of the art of non-invasive blood glucose analysis. The methodology taught in U.S. patent application Ser. No. 08/820,378 is performed by the apparatus taught in U.S. patent application Ser. No. 08/816,723, and each of these references is herewith incorporated by reference.

By way of introduction, the methodology taught in U. S. patent application Ser. No. 08/820,378 is introduced as follows.

Any object at a temperature above absolute zero (−273.16 degrees Celsius) emits infrared energy. The energy density of such emissions is described by Planck's law and are often referred to as a blackbody curves. Theoretically, a body with emissivity 1.0 would exhibit this emission spectra according to Planck's Equation. Many objects have emissivities close to 1.0. Human tissue for instance has an emissivity of approximately 0.9 to 0.98. It is well known that infrared emissions from the human body obey Planck's law and yield a black body type emission spectra.

Although a human body may emit energy that follows Planck's Equation, Planck's Equation does not completely describe the sum total of all energy emitted from a human body for two reasons:

1. The layers of the tissue and body fluids are selectively absorptive to some wavelengths of infrared energy. Thus, layers of tissue and blood or other fluids may selectively absorb energy emitted by the deeper layers before that energy can reach the surface of the skin.

2. There is a temperature gradient within a body, the deeper layers being warmer than the outer layers, which causes further deviation from the theoretical black body emissions.

Whenever these two conditions exist naturally, or can be forced to exist, the inventors have determined that a composition-dependent absorption spectra can be constructed from proper analysis of the total energy emitted from the body. For heterogeneous bodies, composition may be depth dependent and conversely, absorption spectra generated from deeper layers can contain sufficient composition information to allow quantification of the concentrations of individual constituents at that depth into the tissue. This is possible when a temperature gradient either occurs or is induced in the body. The slope of the temperature gradient is such that the temperature is cooler at the surface of the body closer to an infrared detector than at a more distant location from the detector, typically deep within the body.

The invention taught in U.S. patent application Ser. No. 08/820,378 uses the natural temperature within the body as the source of the infrared emissions. As will be explained in more detail below, as these deep infrared emissions pass through layers of tissue that are at a lower temperature than the deeper emitting layer, they are selectively self absorbed. This selective self-absorption produces bands of reduced energy in the resulting emission spectra when the energy finally exits the material under study. The spectra containing the bands where energy has been self absorbed is called an absorption spectra.

The invention taught in U.S. patent application Ser. No. 08/816,723 employs cooling to promote "self-absorption" by letting the temperature gradient propagate to selected layers typically between 40 and 150 microns below the surface. When the temperature gradient has sufficiently propagated, the techniques presented therein can non-invasively deliver absorption spectra of the tissue, blood, and interstitial fluid containing glucose. The inventions incorporated by reference can deliver precise information about the composition of individual layers deep within a heterogeneous body of material by measuring the absorption spectra at different times as a temperature gradient propagates from the surface to deep within the material under test.

According to Ser. No. 08/820,378, there is provided a spectrometer for the non-invasive generation and capture of thermal gradient spectra from human or animal tissue. The spectrometer includes an infrared transmissive thermal mass for inducing a transient temperature gradient in the tissue by means of conductive heat transfer with the tissue, and cooling means in operative combination with the thermal mass for cooling the thermal mass.

Also provided is an infrared sensor means for detecting infrared emissions emanating from the tissue as the transient temperature gradient progresses into the tissue, and for providing output signals proportional to the detected infrared emissions. Data capture means is provided for sampling the output signals received from the infrared sensor means as the transient temperature gradient progresses into the tissue.

The invention of Ser. No. 08/820,378 also provides a method for the non-invasive generation and capture of thermal gradient spectra from living tissue. The method comprises the steps of:

cooling an infrared transmissive mass;

placing the infrared transmissive mass into a conductive heat transfer relationship with the tissue, thereby generating a transient temperature gradient in the tissue;

detecting infrared emissions emanating from the tissue and passing through the infrared transmissive mass;

providing output signals proportional to the detected infrared emissions; and sampling the output signals as the transient temperature gradient progresses into the tissue.

In one preferred embodiment taught in Ser. No. 08/816, 723 a germanium cylinder, cooled to 0° C., is brought into intermittent contact with the patient's warm skin, and the resulting thermal gradients so formed are used to perform the methodology taught in Ser. No. 08/820,378. Skin warming, according to this invention, may be accomplished by simply allowing the patient's skin to naturally re-warm between cooling contact. Alternatively, an external heat source in the form of a second, warmer germanium cylinder may be utilized to facilitate skin warming. The intermittent heating and cooling of the patient's skin results in the creation of transient thermal gradients. In this manner, useful spectra are generated which in turn yield very good measurements of the patient's blood glucose levels.

While the methodology taught in the incorporated references presents a significant advance in non-invasive glucose metrology, there exists room for further improvements.

One such improvement lies in the manner in which the data collected by the apparatus are manipulated. In the methodology taught in Ser. No. 08/820,378 a volts-to-watts radiometric calibration step is often required. To preclude this requirement, the teachings of U.S. Pat. No. 6,161,028 were developed; this patent is herewith incorporated by reference. The methodology taught therein takes advantage of the fact that by inducing a temperature gradient, a difference parameter between the signal at a reference wavelength and the signal of an analyte absorption wavelength may be detected. The frequency or magnitude or phase difference of this parameter may be used to determine analyte concentration. A further object of the invention taught therein is to provide a method of inducing intermittent temperature modulation and using the frequency, magnitude, or phase differences caused by analyte absorbance to determine analyte concentration. This intermittent temperature may be periodic or a periodic.

One improvement to the apparatus taught in Ser. No. 08/816,723 enables the methodology taught in U.S. Pat. No. 6,161,028 to be performed. To enable this latter methodology, a fairly rapid series of measurements is taken. While the non-solid-state apparatus taught in Ser. No. 08/816,723 is capable of cycle frequencies of 2 Hz, an apparatus which seeks to implement measurements based on phase differences can, with good effect, make use of much faster cycle frequencies. Faster cycle times equate to faster measurements, and less patient waiting time. An apparatus which enables faster repetitive measurements or cycle times will accordingly enable these advantages.

An additional advantage of the method taught in U.S. Pat. No. 6,161,028 is that by using a periodically modulated temperature gradient, surface skin effects may be measured and corrected for. Another improvement lies in the nature of the contact between the germanium cylinder and the patient t s skin. It is possible that some apparatus performing subsurface thermal gradient spectrometry may require more than one measurement cycle, or "thump". Where this requirement exists in an apparatus requiring intermittent contact between the patient's skin and heat transfer cylinder one possible source of error exists in the nature of this contact. If several measurement cycles are required to effect an accurate measurement of blood glucose, it follows that the cylinder must be brought into contact with the skin several times. The problem is that each of such contacts tends to be slightly different. Slight differences in pressure at the skin/cylinder interface occur. The patient may move that portion of his or her body, for instance the arm, in contact with the apparatus. Muscular tension may change from reading to reading. Each of these factors, and perhaps others as well, tend to complicate the already complex nature of the contact between the skin and the cylinder. A significant improvement will result if these "rheological effects" can be controlled or standardized if not altogether eliminated.

Closely related to the rheological effect problems previously enumerated is the intermittent nature of the thermal/mechanical/optical interfaces occasioned by the intermittent nature of several of the thermal, mechanical, and optical elements of the apparatus taught in Ser. No. 08/816,723.

Yet another improvement could be made to the apparatus taught in Ser. No. 08/816,723, which relates to a methodology which would perform at least one of the previously discussed subsurface thermal gradient spectrometric methodologies, and which could be reliably performed on an apparatus having no moving parts whereby the thermal gradient is generated and captured.

From the foregoing, advances in the field of non-invasive analyte determinations may be had by an apparatus which supports the methodology taught in U.S. Pat. No. 6,161,028, as well as other subsurface thermal gradient spectrometric methodologies including but not necessarily limited to those discussed in U.S. patent application Ser. Nos. 08/820,378 and 08/816,723. An apparatus which enabled more rapid measurement cycle times would not only do much to support the new methodology, but would lessen patient waiting time and improve measurement accuracy. One possible methodology which could provide such advantages would be to form a measuring device which does not rely on a mechanically intermittent device, such as the one taught in U.S. patent application Ser. No. 08/816,723 but which generates transient thermal gradients in a "solid state" manner: i.e., without the mechanical moving of a cooling/measuring cylinder into and out of contact with the patient's skin. Such a solid state device would present the further advantages of leaving intact the thermal, mechanical, and optical interfaces intact, minimizing the rheological effects of intermittent cylinder/skin contact.

Such a system, however, poses a very difficult problem: If the device is left in intimate contact with the patient's skin, it naturally follows that the same element will be used to both cool the skin and to take readings from it. Moreover, to increase cycle times, it may be necessary to provide an external warming to the skin. From this it follows that the same structure will be required to alternately warm the skin, cool the skin, and measure the thermal gradient so induced. Given that the element must perform each of these functions, the cool cylinder must be protected from unwanted warming. The warming function must be performed accurately without undue influence from the cooling function. Finally, could either be performed while measuring the transient thermal gradients so generated?

SUMMARY OF THE INVENTION

The present invention teaches a solid state non-invasive infrared absorption spectrometer for the generation and capture of thermal gradient spectra from living tissue. As used herein, the term "solid state" is defined to mean that the apparatus has no moving parts which move with respect to one another to effect the creation of the transient thermal gradient, or which affect the infrared spectroscopic measurement taken in response to the creation of such a gradient. Moreover, a solid state system is one in which the thermal gradient-inducing device is brought into contact with the patient's arm, and left in such contact during the entire measurement series. To achieve the novel advantages obtainable from such a solid state device, the spectrometer includes an infrared transmissive thermal mass, or window, for inducing a transient temperature gradient in the tissue.

In place of the intermittent physical contact taught by U.S. patent application Ser. No. 08/816,723, the present invention utilizes a single thermal mass structure, referred to as a thermal mass window, which not only heats and cools the patient's skin to affect the transient thermal gradient, but through which are also transmitted the absorption spectra generated by the gradient. Accordingly, the thermal mass window of the present invention remains in contact with the patient's skin during the time the measurement is made, thereby minimizing intermittent rheological factors.

The thermal mass window includes an infrared transparent window in operative combination with an intermittent heat exchanger for intermittently inputting heat into the window. The thermal mass window is urged into contact with the patient's skin and is thus utilized to conductively and intermittently cool and warm the patient's skin. The cooling function may be implemented solely by the relatively large, cool thermal mass of the thermal mass window itself. Alternatively, heat can actively be withdrawn from the window by means of a cooling device which intermittently removes heat from the window. The cooling device may be a separate unit from the heat exchanger, or may be incorporated therewith. This intermittent warming and cooling of the skin may be periodic or a periodic.

In one embodiment of the present invention, the thermal mass window is implemented to include a plurality of zones disposed in or on the thermal mass window. In this embodiment the thermal mass window includes a first zone characterized by high thermal conductivity for cooling the thermal mass and hence the patient's skin, and a second zone characterized by high thermal conductivity in operative combination with the first zone of high thermal conductivity, which second zone provides conductive heat transfer with the patient's skin. The second zone is preferably of relatively small thermal mass, while the first zone is preferably of relatively large thermal mass. The present invention teaches a number of methodologies for forming the thermal mass window. Each of the zones is optically transparent in the infrared.

One methodology incorporates a third zone characterized by low thermal conductivity which is disposed between the first and second zones, which third zone serves to thermally isolate the first and second zones from one another. Indeed, this third zone can be said to be a thermal impedance zone. The third zone, like the first and second zones, is optically transparent in the infrared. And like the second zone, it is preferably, but not necessarily, of small thermal mass.

Disposed on an outer surface of the second zone is a heater for evenly and accurately heating the patient's skin. The first zone may be in substantial thermal contact with a heat exchange body which, in combination with the mass of the first zone itself, serves to cool the entire thermal mass window. Accordingly, the present invention contemplates a window where heat is intermittently added to the second zone, and withdrawn from the first. The second zone serves to thermally isolate the first and third zones from one another. Each of the zones, being optically transparent, at least in the infrared, enables optical transmission through the entire thermal mass window.

The device taught herein may incorporate a heat exchanger, or may have no heat exchanger at all. Where a heat exchanger body is implemented, it may be cooled actively or passively. In one embodiment of the present invention, active cooling is achieved by providing a flow of cooling water to the heat exchanger body. Of course, alternative active or passive cooling methodologies, well within the ability of one having ordinary skill in the art, could be implemented with equal facility. In another embodiment of the present invention, there is provided no heat exchanger. In this embodiment, the thermal mass window has sufficient thermal capacity or mass that the temperature of the device as it is cycled rises sufficiently slowly during the measurement cycle that the temperature rise over time can be compensated for. Research indicates that some such embodiments may function properly for several minutes before the temperature rise becomes uncontrollable.

Where a structure is maintained in contact with the ambient atmosphere at an artificially depressed temperature, condensation can be a problem. To alleviate this problem the housing surrounding the window and heat exchanger can be equipped with any of several methodologies to prevent condensation from forming on one or more of the relatively cool surfaces. In one embodiment of the present invention, there are provided at least one of an electro-thermal heater and a flow of dry purge gas to keep one or more surfaces of the window free of condensate. Alternative methodologies for the prevention of condensation, including the use of chemical surfactants, may with equal facility be implemented.

Also provided is an infrared sensor device for detecting infrared emissions emanating from the tissue as the transient thermal gradient progresses into the tissue, and for providing output signals proportional to the detected infrared emissions.

A data capture device is further provided for sampling the output signals received from the infrared sensor device as the transient temperature gradient progresses into the tissue.

Other features of the invention are disclosed or apparent in the section entitled "BEST MODE OF CARRYING OUT THE INVENTION".

BRIEF DESCRIPTION OF THE DRAWINGS

For fuller understanding of the present invention, reference is made to the accompanying drawings in the following detailed description of the Best Mode of Carrying Out the Invention. In the drawings.

Figure 1:
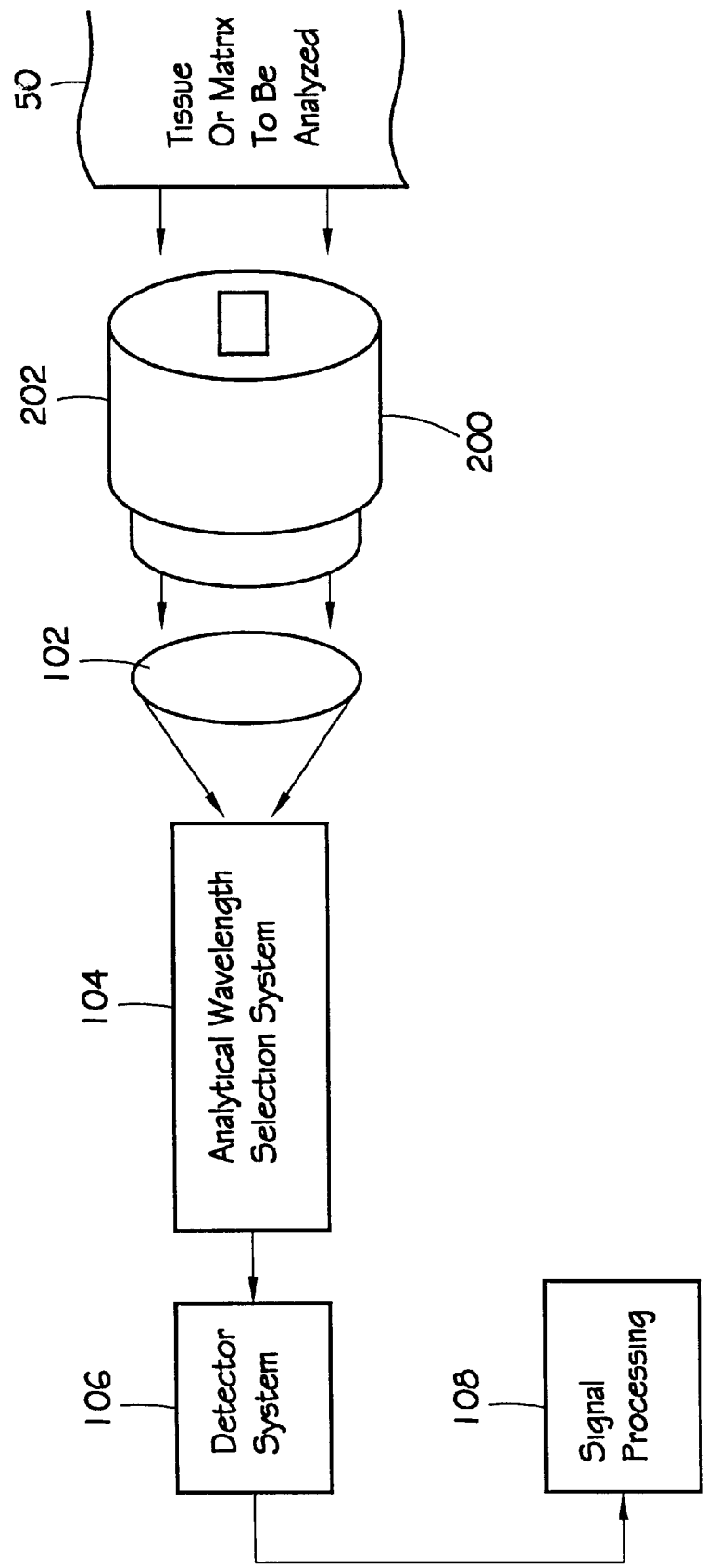
FIG. 1 is a conceptual representation of a first spectrometer formed in accordance with the present invention.

Reference numbers refer to the same or equivalent parts of the invention throughout the several figures of the drawing.

BEST MODE OF CARRYING OUT THE INVENTION

The present invention relates to the measurement of infrared energy absorption in a heterogeneous body. The following description is presented to enable one of ordinary skill in the art to make and use the invention as provided in the context of a particular application and its requirements. Various modifications to the preferred embodiments will be readily apparent to those skilled in the art, and the generic principles defined here may be applied to other embodiments. Thus, the present invention is not intended to be limited to the embodiments shown, but is to be accorded the widest scope consistent with the principles and novel features disclosed herein.

A discussion of the principles of non-invasive infrared spectrometry applied to analyte quantification can be found in the incorporated references.

The mechanism or process taught herein for creating and controlling the magnitude, propagation velocity and contour profile of the thermal gradient incorporates cyclic cooling and re-warming of the observation site. The mechanism or process for cooling the surface of the tissue target site is unique in the present invention not only in that the cooling body becomes part of the optical pathway through which the infrared energy must pass in order to be recorded, but that this cyclic cooling and re-warming is achieved using a solid state system. The present invention is suitable for analyses conducted in accordance with the incorporated references, as well as other applications apparent to those having ordinary skill in the art.

To improve the signal-to-noise ratio in the measurement it may be advisable to repeatedly observe the depth-selective spectral emissions. The device taught herein is designed to repetitively and repeatably cool and re-heat the target tissue area without the need to mechanically remove one or more thermal masses from the patient's skin. This not only results in a simpler system than taught in U.S. patent application Ser. No. 08/816,723, but reduces the rheological effects inherent in that design. Most importantly, the device taught here provides the capability to very rapidly cycle between heating and cooling with a frequency of between about 0 and about 20 Hz.

Uniformity of the heating and cooling across the surface area of the target tissue and within the volume under the target site is also an important parameter for maximizing the spectral signal content of the depth dependent emissions. Reduced uniformity of the temperature across the surface during either heating or cooling will result in the thermal gradient profile not being uniform in a direction perpendicular to the surface. The resulting absorption spectra will contain absorption information from differing depths across the surface of the target thus losing specificity between spectral content change and depth.

Referring to FIG. 1, a block diagram of a first preferred embodiment of the present invention is shown. In this embodiment there is provided a thermal gradient device 200 for inducing a temperature gradient within the body 50. Infrared emissions from the body 50 are transmitted through thermal gradient device and are then collected by an optical collector 102. A particular wavelength is selected that corresponds to a particular constituent in the body 50 by a wavelength selection system 104. A detector 106 receives information from the selection system 104. A signal processing system 108 processes the information. The several elements of the system will be described below.

Thermal Gradient Device 200

Figure 2:
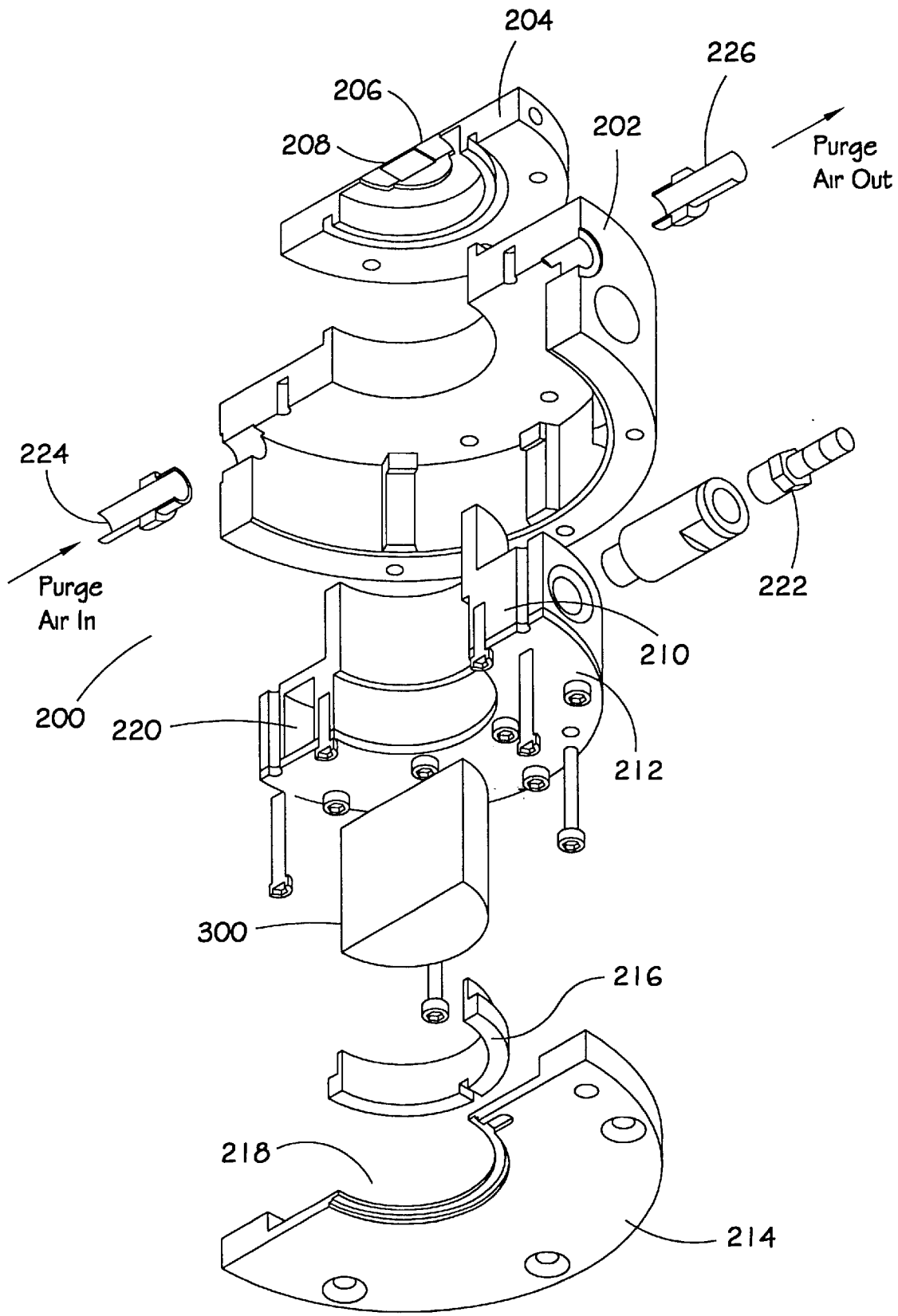
FIG. 2 is a cutaway exploded view of the thermal gradient device constructed in accordance with the present invention.

In one preferred embodiment of the present invention, as shown at FIG. 2, the thermal gradient device 200 includes a housing 202. Housing 202 may be formed of injection-molded plastic, or other materials which will retain the several elements of device 200 therein while minimizing movement of those several elements, and minimizing condensation thereon. Disposed on an upper surface of housing 202 is window holder 204. Window holder 204 may be formed of similar material to housing 202. Window holder 204 defines aperture 206. Sealing aperture 206 is window 208, which is formed of polycrystalline float zone silicon. Window 208 may be attached substantially as shown to housing 202, or in the alternative may be a replaceable and/or disposable element, attachable to and detachable from housing 202 or to window holder 204 disposed thereon.

Disposed within housing 202 is heat exchanger body 210, retained in position within housing 202 with a plurality of fasteners, for instance socket headed cap screws 212. Disposed within heat exchanger body 210 is a thermal mass window 300, more fully described below. Heat exchanger body 210 is preferably formed of copper, one of its alloys, or another material having thermal mass and good thermal transmissive qualities, and preferably good resistance to corrosion. In one embodiment of the present invention, heat exchanger 210 is a hollow structure, defining cavity 220. Cavity 220 is provided with a continuous flow of chilled water by means of a pair of water fittings, one of which is shown at 222. Thermal mass window 300 is chilled by heat exchanger body 210. In one preferred embodiment this cooling is to approximately 10° C., but other temperatures may, with equal facility, be implemented for certain metrologic reasons in some applications. This depressed temperature provides an enhanced temperature gradient at the measurement site to enhance the infrared signal to allow detection by detectors (not shown in this view).

Heat exchanger body 210 is typically connected to a water bath such as a LAUDA model RM-20 (not shown). The water bath is operated at 10° C. and the bath's internal circulating pump circulates water inside the heat exchanger to cool thermal mass window 300. Alternatively, thermal mass window 300 can be cooled with a thermoelectric cooler such as Mellcor (Trenton, N.J.) FCO.6 controlled by an Alpha Instruments (Johnston, R.I.) TEC controller, again not shown. Additional means for cooling the target surface include cold $N_2$ or other gases, as well as infrared transmissive cooling fluids circulated immediately in contact with target window rear surface. Waste heat can be dissipated in a phase change material such as TEAP 29, manufactured by PCM Thermal Solutions of Naiperviile, Ill. These and other alternative cooling methodologies, well within the purview of one having ordinary skill in the art, may of course be utilized.

In at least one other embodiment of the present invention, there is provided no heat exchanger. In this embodiment, the thermal mass window has sufficient thermal capacity or mass that the temperature of the device as it is cycled rises sufficiently slowly during the measurement cycle that the temperature rise over time can be compensated for. Research indicates that some such embodiments may function properly for several minutes before the temperature rise becomes uncontrollable.

A bottom cover 214 is retained with fasteners, not shown in this view, to housing 202. Bottom cover 214, in operative combination with window holder 204, serves to seal the several elements of thermal gradient device 200 within housing 200, minimizing contamination and condensation. Thermal mass window 300 is retained within heat exchanger body 202 and bottom cover by means of retaining ring 216, which both seals thermal mass window 300 within aperture 218 of bottom cover 214, but urges thermal mass window 300 into intimate thermal contact with both heat exchanger body 210, and window holder 204.

Since the temperature of the thermal mass window 300 may be below the dew point, special precautions in some embodiments must be taken to assure that no condensation exists on any surface through which infrared energy is collected. This necessitates either dehumidified enclosures, mechanical defrosting of the crystal surfaces or chemical means for dew prevention. In a first preferred embodiment of the present invention, condensation is prevented at the upper end of the thermal gradient device by means of a flow of purge gas, for instance dry nitrogen, into housing 202 through a pair of purge gas fittings 224 and 226. Disposed on bottom cover 214 there is provided an electrical heater (not shown) for preventing fogging of the bottom of thermal mass window 300. Again, alternative condensation prevention methodologies, well known to those having ordinary skill in the art, may be employed. Moreover, in some applications either or both condensation prevention methodologies may not be required, and may therefore be dispensed with.

Thermal Mass Window

Figure 3:
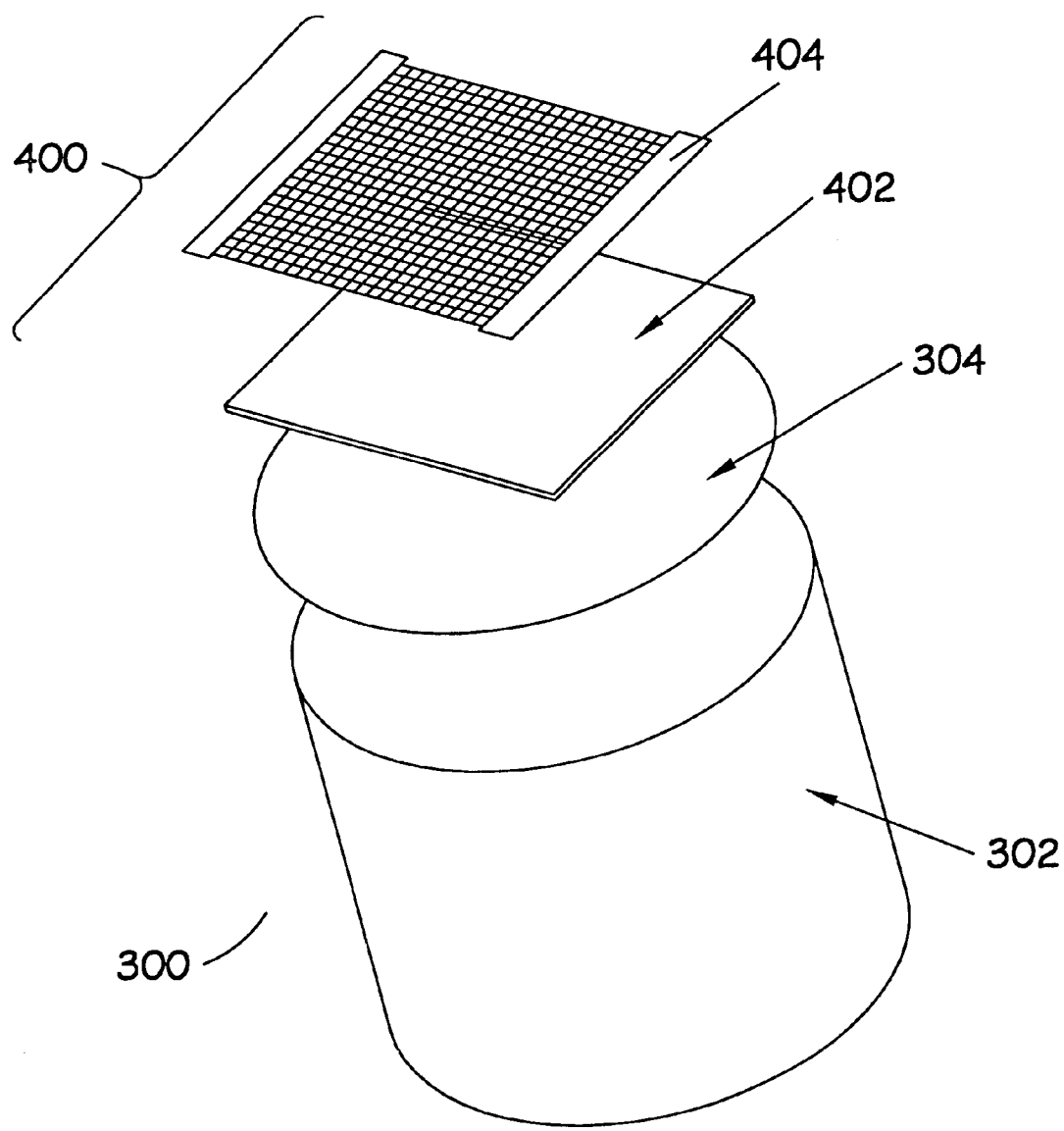
FIG. 3 is an exploded view of a thermal mass window.

Referring now to FIG. 3, one embodiment of thermal mass window 300 is shown. Thermal mass window 300 comprises a first zone of high thermal conductivity, in this embodiment as a germanium cylinder 302 defining the previously discussed first zone. Germanium cylinder 302 is a germanium crystal, for instance as manufactured by Meller Optics of Providence, R.I., and is 19 mm in diameter and 19 mm in length. Alternative dimensions may of course be implemented. Both end surfaces are "polished to optically flat condition". Other materials, geometries, surface textures, and sizes are acceptable. In particular, the present invention specifically contemplates the use of silicon and diamond as thermal mass window elements. The thermal mass window's function is threefold. One function is to cool the measurement "site", another to warm it, and the last is to efficiently collect and transmit the infrared energy to the collector and detector systems.

Disposed upon an upper surface of germanium cylinder 302 is a third zone having low thermal conductivity, defining a thermal impedance zone 304. In this embodiment, a 50 μm layer of AMTIR-1, a $Ge_{33}As_{12}Se_{55}$ glass, is utilized. AMTIR-1 is available from Amorphous Materials Inc., 3130 Benton, Garland, Tex. 75025, and the description of AMTIR-1 found on that firm's material safety data sheet for this material is hereby incorporated by reference.

Further disposed on an upper surface of thermal impedance zone 304 is a thermo-electric heater 400, including substrate 402 and a heating element 404. In this embodiment, substrate 402 defines the previously discussed second zone, which second zone is characterized by high thermal conductivity. In this exemplar, substrate 402 is formed as a layer of polycrystalline float zone silicon, 0.25 mm in thickness. Disposed on an upper surface of substrate 402 is heater element 404, further described in FIG. 4.

It should be noted that the principles of the present invention specifically contemplate several methodologies for the formation of thermal mass window 300. As a result, the previously discussed zones may be implemented as discrete layers, substantially as shown in FIG. 3. The implementation of such layers may be by means of lamination, chemical deposition including vapor deposition and liquid deposition, crystal growth, epitaxial growth, coating, or other layer formation methodologies well known to those having ordinary skill in the art.

Particularly well suited for forming several of the embodiments of the present invention are well known integrated circuit fabrication methodologies including, but specifically not limited to, those previously discussed. A generalized discussion of these methodologies may be found in *Microchip Fabrication, A Practical Guide to Semiconductor Processing*, $3^{rd}$ Ed., Peter Van Zant, McGraw Hill, 1997, which is herewith incorporated by reference.

A further alternative contemplates the formation of discrete zones which are not specifically layers in the strict sense of the word, but are defined as specific regions having the previously discussed properties. Such zones could be formed by doping one or more zones with a dopant, or by sintering materials having specific thermal transmissive properties, thereby resulting in a zone having the requisite properties.

Figure 4:
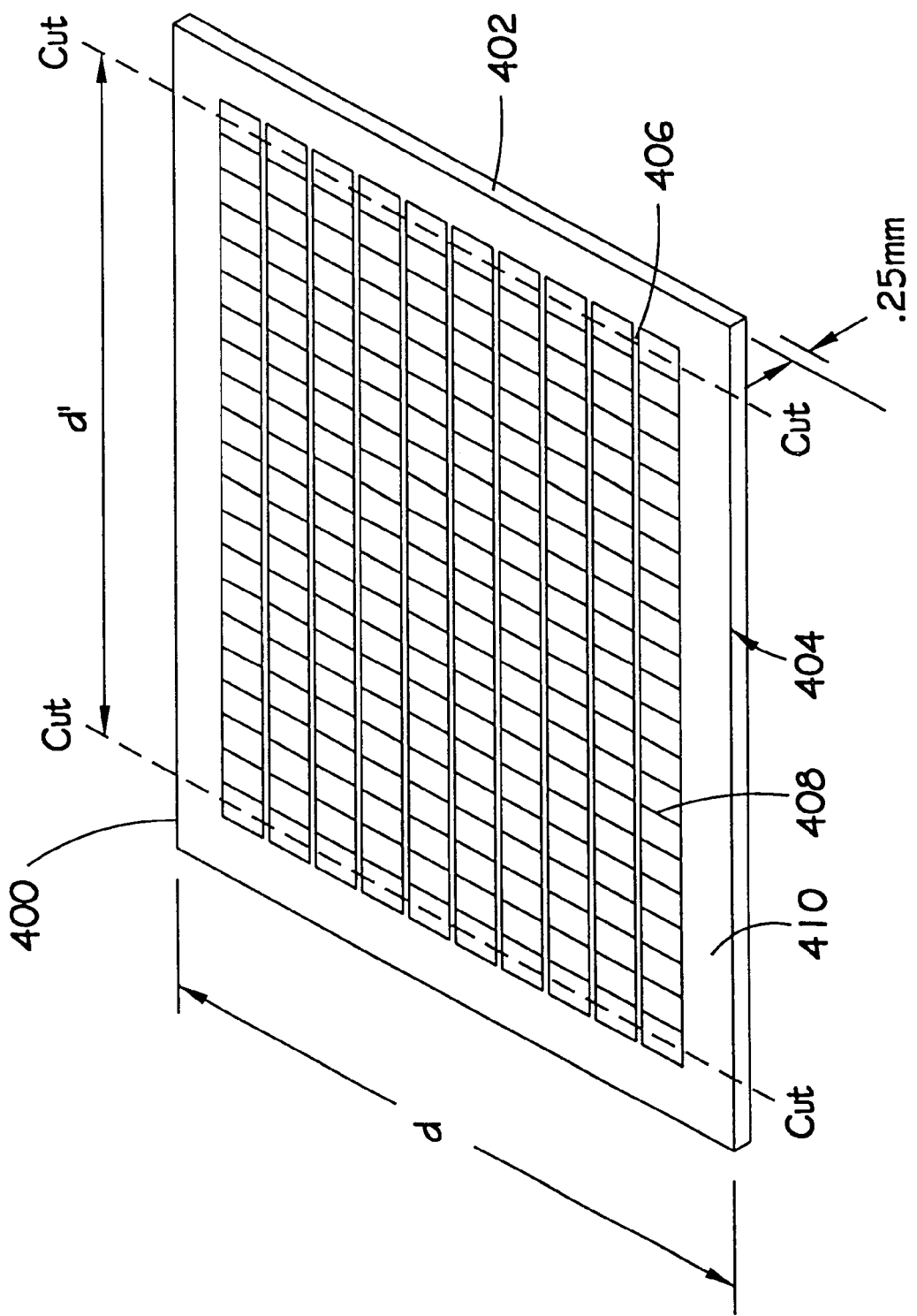
FIG. 4 is a perspective view of the wire grid electrical heater of the present invention.

Referring now to FIG. 4, the embodiment of heating element 404 formed as a 1 μm thick layer of gold or platinum deposited over a 300–500 Å thick adhesion layer of 10/90 titanium/tungsten alloy applied to substrate 402 is shown. Either or both of the gold or platinum layer, hereafter referred to as the gold layer, and the alloy layer may be deposited by chemical deposition including vapor deposition and liquid deposition, plating, laminating, casting, sintering, or other forming or deposition methodologies well known to those having ordinary skill in the art. After gold/alloy deposition, those materials are formed into a wire bridge heating grid as described below. Alternative heating element materials are specifically contemplated by the teachings of the present invention.

Having continued reference to FIG. 4, after gold/alloy deposition, the gold/alloy layers are formed into the wire bridge heating grid shown in that figure. Forming of the grid may be by means of masking, chemical etching, photo etching, ion etching or milling, abrasive etching, grinding or other material formation or removal methodology well known to those having skill in the art. In one embodiment of the present invention, the gold/alloy layer is etched back to form a plurality of sub-busses 406. In this embodiment sub-busses 406 are 50 μm wide traces on 1mm centers. Bridging sub-busses 406 are a further plurality of heating wires 408, formed as 20 μm wide traces on 5 mm centers.

In this preferred embodiment in FIG. 4, substrate 402 is initially formed as a square having sides of length "d", in this case 12 mm. Following the material deposition and etching back previously discussed, substrate 402 is cut back on two opposite sides as shown to form heater 400 including busses 410. At this juncture, heater 400 forms a rectangle having dimensions d by d', in this embodiment 12 mm×10 mm. This particular configuration is suitable to one preferred embodiment of the present invention. It will be apparent to those having ordinary skill in the art that alternative alloys, coatings, dimensions, geometries, spacings and bus configurations may, with equal facility be implemented for this or other specific applications. The principles of the present invention specifically contemplate all such alternatives.

Busses 410 are in electrical combination with a switched power supply, not shown. The power supply is further in operative combination with a timed switching device or system control, again not shown, for intermittently applying electrical power to heater 400. As previously discussed, this intermittent application of electrical power may be periodic or a periodic in nature.

Figure 7:
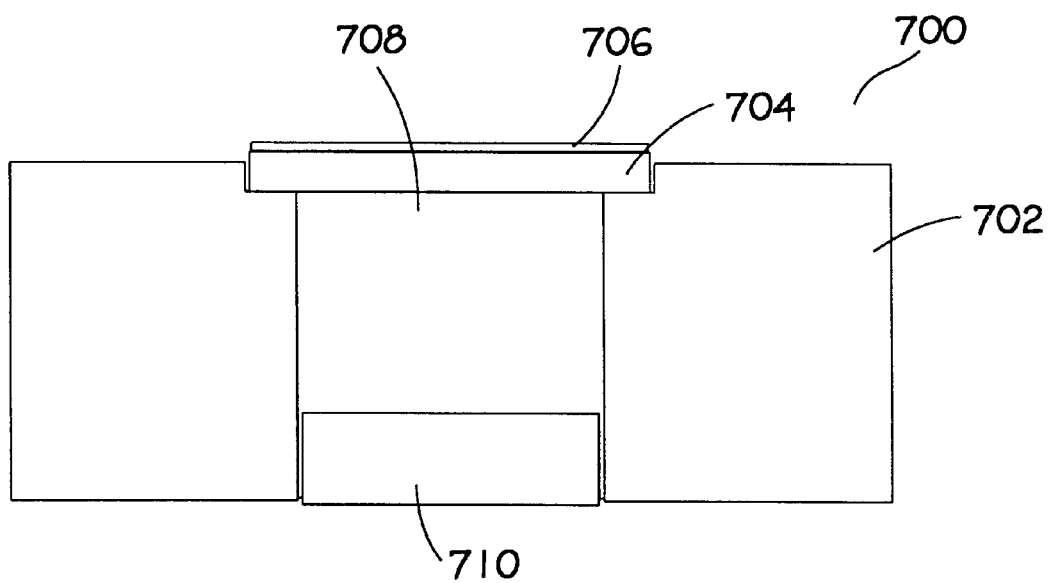
FIG. 7 is a cross-sectional view of an alternative thermal mass window.

An alternative to this embodiment of thermal mass window 300 is shown as thermal mass window 700 in FIG. 7. Having reference to that figure, thermal mass window 700 comprises an infrared transparent window 704, relatively thin and of less thermal mass in comparison to window 302, previously discussed. Window 704 is in substantial thermal contact with a heat sink 702. In this embodiment, heat sink 702 takes the form of a cylinder of copper which in turn defines an axial cavity 708. Covering one end of axial cavity 708 is window 704. Disposed upon one surface of window 704 is a heating element 706, formed as previously discussed. In this simplified cross section, element 710 represents the "back end" of a spectrometer implementing this version of the thermal mass window. Back end 710 comprises those elements of the spectrometer optically downstream from the thermal mass window 700, including but not necessarily limited to optical collection system 102, analytical wavelength selection system 104, detector system 106 and signal processing system 108. In this exemplar, at least one of the foregoing elements may be disposed within heat sink 702, but alternative arrangements are contemplated by the teachings of the present invention.

In this embodiment in FIG. 7, the thermal mass of heat sink 702 serves to cool window 704. The cooling of heat sink 704 may in turn be passive, or active, as previously discussed.

Figure 8:
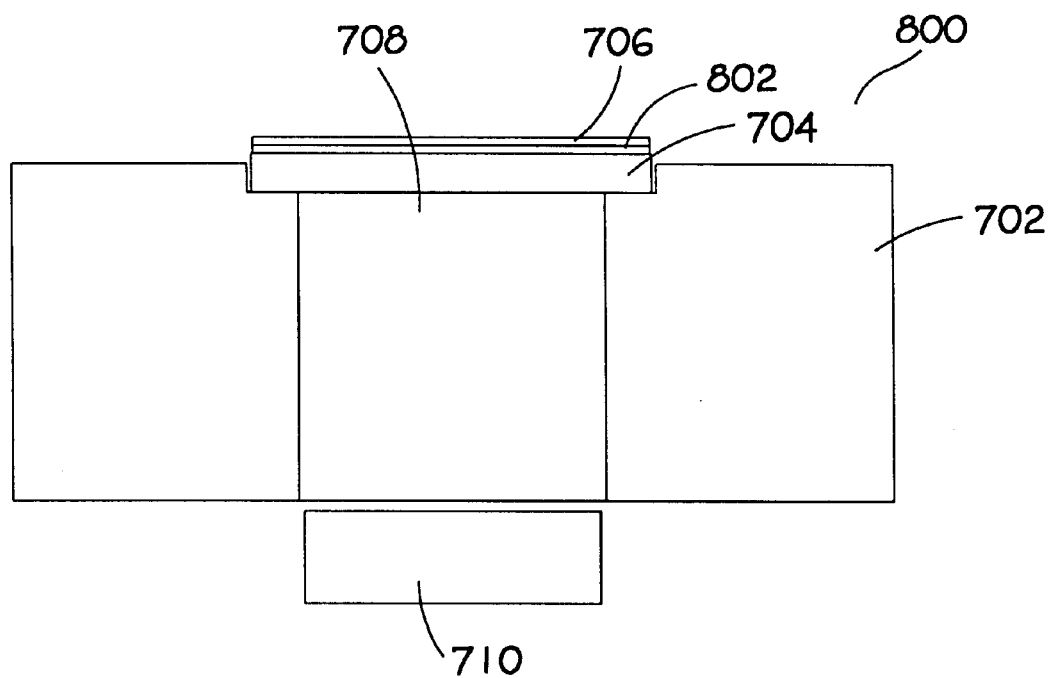
FIG. 8 is a cross-sectional view of another alternative thermal mass window.

A further alternative embodiment is shown at FIG. 8 as 800. This alternative is substantially similar to the embodiment shown in FIG. 7, with the addition of a thermal impedance layer 802 disposed between window 704 and heating element 706. In this embodiment, back end 710 is shown external to heat sink 702, but again, the previously discussed arrangement whereby one or more back end elements is disposed within cavity 708 may, with equal facility, be implemented.

Figure 9:
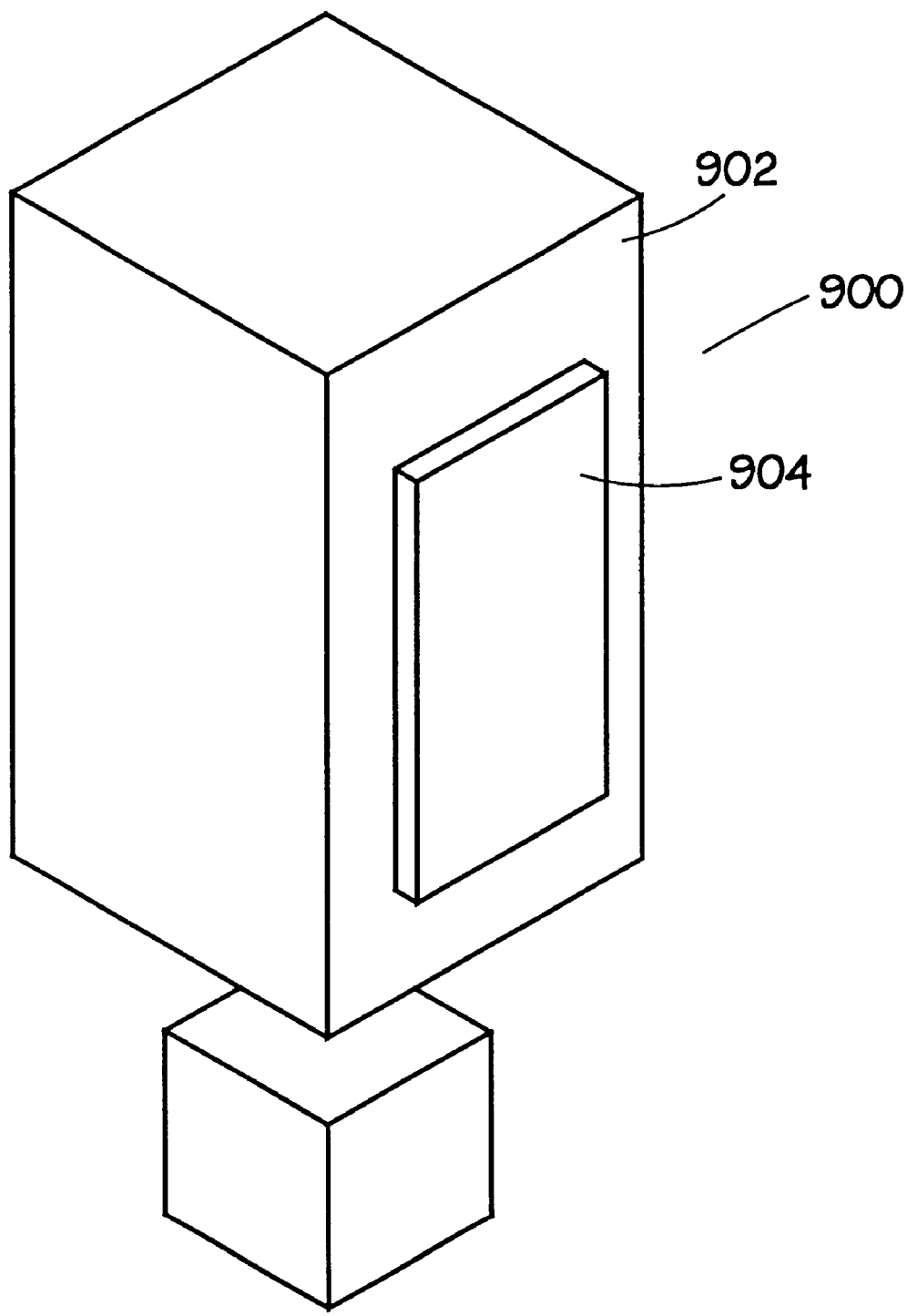
FIG. 9 is a cross-sectional view of yet another alternative thermal mass window.

Yet another alternative embodiment is shown at FIG. 9 as 900. The previous alternatives utilized a plurality of zones to perform the intermittent heating and cooling required to generate thermal gradients. This embodiment utilizes a single thermal mass of infrared-transparent material 902 to both heat and cool the sample under observation. Having reference to FIG. 9, thermal mass window 900 is formed of a mass 902 of infrared-transparent material. As before, a preferred embodiment of this invention contemplates the use of germanium, silicon, or diamond. Alternative infrared-transparent materials may of course be utilized. To apply or withdraw heat from the sample under observation, mass 902 is heated or cooled by means of heat exchanger 904 which is urged into thermal and mechanical contact with mass 902. The alternative heating and cooling of mass 902 is accomplished by means of alternately heating and cooling heat exchanger 904. This heating and cooling may be achieved by any of several known heat-transfer technologies including, but not limited to: the application of a flow of heating/cooling fluid or gas to heat exchanger 904; thermoelectric heating and/or cooling implemented at heat exchanger 904; the use of radiation, especially microwave radiation; and other well-known heat transfer methodologies. The principles of the present invention specifically contemplate all such alternatives.

Analytical Wavelength Selection System 104

Several means of selecting the analytical wavelengths can be used, including but not necessarily limited to:

Discrete infrared bandpass filters;
An interferometer;
A spectrophotometer;
A grating monochrometer, and
A variable filter monochrometer.

In the preferred embodiment, a set of nine discrete analytical filters manufactured by Optical Coating Laboratories Inc. (Santa Rosa, Calif.) are used. In an alternate embodiment a PERKIN ELMER (England) System 2000 Fourier Transform Infra Red Spectrophotometer (FTIR) is used in place of the filters. The filters provide a compact system that is rugged and relatively economical. The use of a specific set of bandpass filters restricts the instrument to analyzing only preselected wavelengths. The use of the FTIR allows the optical measurements of all wavelengths. When using an FTIR, the final analysis wavelengths are selected in the signal processing computer. Therefore an instrument built with discrete filters is dedicated to measuring a predetermined compound, e.g. glucose, while an instrument built using an FTIR can be directed via software modifications to measure any of a number of compounds such as glucose, alcohol, etc.

Detector System 106

The detector system of FIG. 1 converts the infrared energy into usable electrical signals. The detector system 106 typically comprises of two components, an infrared detector and a pre-amplifier.

In the preferred embodiment, the detector is an array of nine Photo Voltaic Mercury Cadmium Telluride (PVMCT) detectors. A detector such as a FERMIOINICS (Simi Valley, Calif.) model PV-9.1 with a PVA481-1 pre-amplifier is acceptable. Similar units from other manufacturers such as GRASEBY (Tampa, Fla.) can be substituted.

Signal Processing System 108

The signal processing system 108 used in the preferred embodiment is a general-purpose programmable personal computer (PC) manufactured by Digital Equipment Corp. (DEC) model 433 1px. Others can be substituted with equal facility. Moreover, a special-purpose computer implemented as hardware, firmware, software or a combination thereof could be devised to perform the specific signal processing functions required. The computer provides a computation engine, display and user interface to the system. An analog-to-digital (A/D) converter system is used to interface the analog signals from the detector to the computer. One such A/D converter is manufactured by Strawberry Tree, Inc. (STI) in San Jose, Calif., as their model "WORKMATE PC".

In the alternate configuration using the FTIR, the Perkin Elmer instrument incorporates a GRASEBY 1×1 MCT detector and includes a computer interface so the Fermionics and STI devices are not required to complete the system.

Operating Sequence

The cycle time of the apparatus is limited only by the time required to propagate a thermal gradient through the patient's skin, and is generally in the range of about 0 to 20 Hz.

When the crystal 300 is in contact with the patient's skin, infrared energy in the 3 to 15 micron band passes from the skin through the crystal 300 and into the Analytic Wavelength Selection System 104. The purpose of the bandpass filter or other similar element, previously discussed, is to select analytical wavelengths. With the proper wavelengths selected, the computation of glucose concentrations based on the theory described above can be accomplished. A typical operating sequence is shown below.

Step 1. Bring chilled thermal mass window in contact with patient's forearm.

Step 2. Energize heater momentarily.

Step 3. Optical energy is detected, selected, and analyzed by the system signal processor to determine glucose concentration per the algorithm discussed in at least one of the incorporated references.

Step 4. Allow chilled thermal mass to re-cool patient's forearm.

Step 5. (Optional, where more than one cycle is required to effect an accurate reading.) Repeat steps 2 through 4 above until the requisite number of separate glucose determinations have been made.

Step 6. Either report the result or, where more than one cycle is required, average all determinations and report result.

The useful range of analytical wavelengths of the present invention is wide. In a sample at room temperature (25° C.), the peak energy is emitted at 9.8 $\mu$m. In the case of a human body (maintained typically at 37° C.), the peak emissions are near 9.3 $\mu$m. Substances at other temperatures have peak emissions at other wavelengths. In the case of room temperature or human body temperature samples, the analytical range containing most of the energy is in the range of 2 to 14 $\mu$m.

Figure 5:
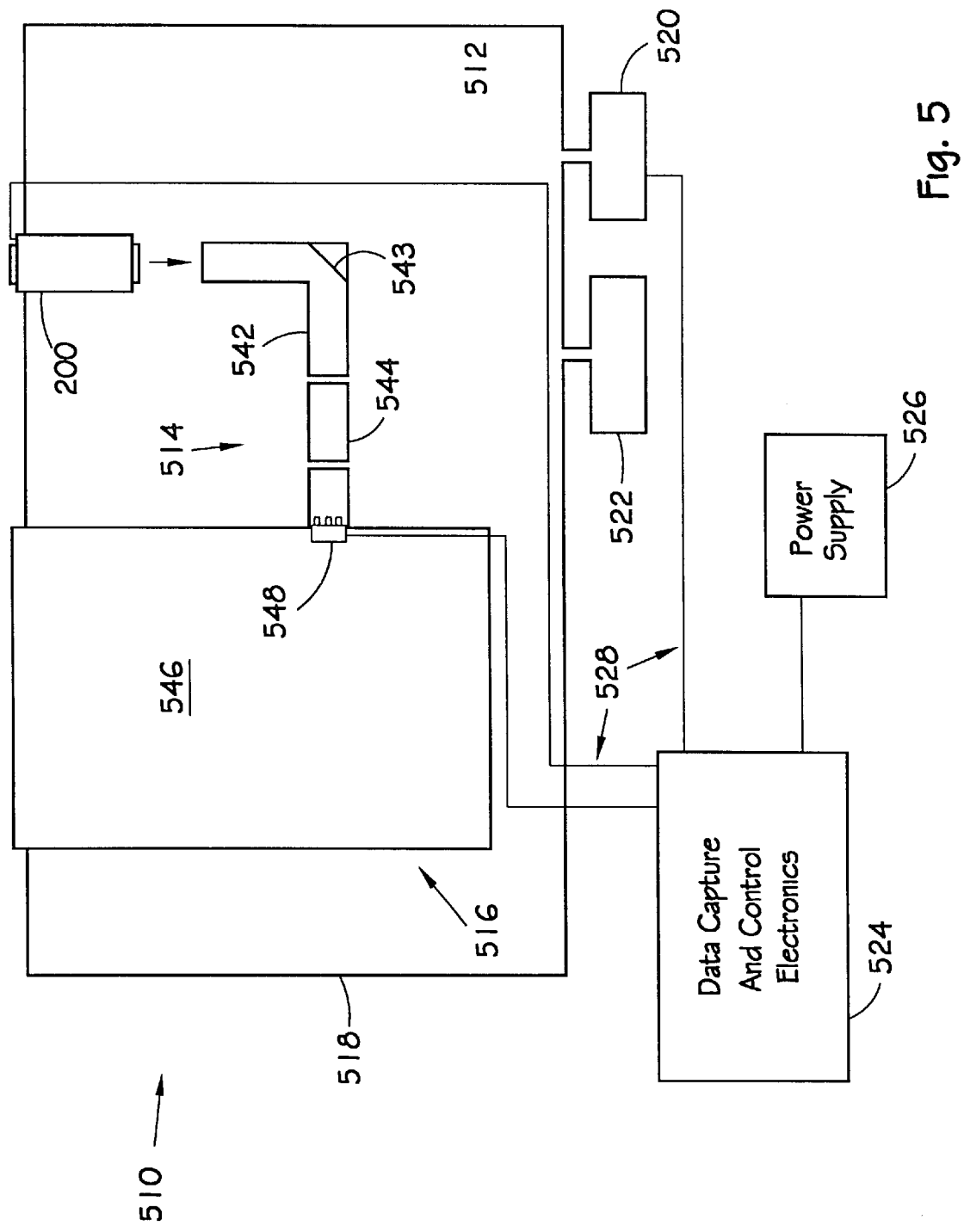
FIG. 5 is a second spectrometer formed in accordance with the present invention.

A second preferred embodiment of a spectrometer according to the present invention, generally indicated by the numeral 510, is illustrated in FIG. 5. The spectrometer 510 comprises a thermal gradient device 200, an optics module 514, an infrared detector subsystem 516, all surrounded by an insulated housing 518. Housing 518 is substantially airtight. In communication with the housing 518 is a dry gas source 522. A data capture and control system 524 and a power supply 526 are coupled to various components of the spectrometer 510 by means of electrical signal and power lines 528. The thermal gradient device 200 has been previously described.

Located below the thermal gradient subsystem 512 is the optics module 514. The optics module 514 consists of an infrared transmission path 542 and an homogenizer 544. Infrared light which has passed through thermal gradient device 200 is passed to the homogenizer 544 by means of the optical transmission path 542. The optical transmission path 542 is provided with a mirror 543 for reflecting the infrared light through a 90° angle.

The homogenizer 544 serves to de-focus the infrared light completely as it passes through the homogenizer 544. This ensures that the sensors in the infrared detector subsystem 516 are equally affected by any non-uniformities present in the infrared light before homogenization.

Infrared light leaving the homogenizer 544 enters the infrared detector subsystem 516. The infrared detector subsystem 516 comprises a dewar vessel 546 and an infrared detector array 548. The dewar vessel 546 is filled with liquid nitrogen to cool the infrared detector array 548.

The infrared detector array 548 comprises nine photovoltaic mercury cadmium telluride (MCT) infrared detectors arranged in a three by three configuration. Located in front of each of the nine infrared detectors in the detector array 548 is a single wavelength infrared filter. Each detector is therefore a sensor for one particular band of infrared energy, and the output of the nine infrared detectors together provides the desired infrared spectrum. In the illustrated embodiment of the invention, the nine sensors are respectively sensitive to infrared energy at 9.23, 10.7, 5.17, 12.0, 6.97, 10.27, 7.31, 6.03 and 8.4 micron wavelengths. Sensors detecting alternative wavelengths may be substituted where a particular requirement exists therefor.

Each of these wavelengths is selected to provide particular information which is relevant to the determination of the composition of the human or animal tissue under analysis. For example, infrared light at the 5.17 micron wavelength transmits well through water. Accordingly, it can be assumed that infrared light at this wavelength comes from deeper within the tissue than the shallow volume through which the induced temperature gradient is propagating, and is thus an indication of the internal temperature of the tissue. For the purposes of subsequent processing of the infrared spectrum measured by the spectrometer 510, it can then be assumed that a black body at this observed temperature is located behind the volume through which the temperature gradient is propagating.

On the other hand, water absorbs infrared energy very well at the 6.03 micron wavelength. Accordingly, almost all infrared energy at this wavelength which originates deeper in the tissue will be self absorbed by the tissue before it reaches the skin surface. Therefore, almost all of the energy at this wavelength originates at the skin surface, and can be used as an indication of the skin surface temperature.

In the measurement of the glucose content in the tissue, the 9.23 micron wavelength is particularly important, as infrared energy is absorbed by glucose at this wavelength. In particular, the amount of the infrared energy absorbed at this wavelength depends on the glucose concentration in the body, and the signal from this detector can thus subsequently be processed in accordance with the principles of transmission spectroscopy theory to yield a value for the glucose content in the body.

Figure 6:
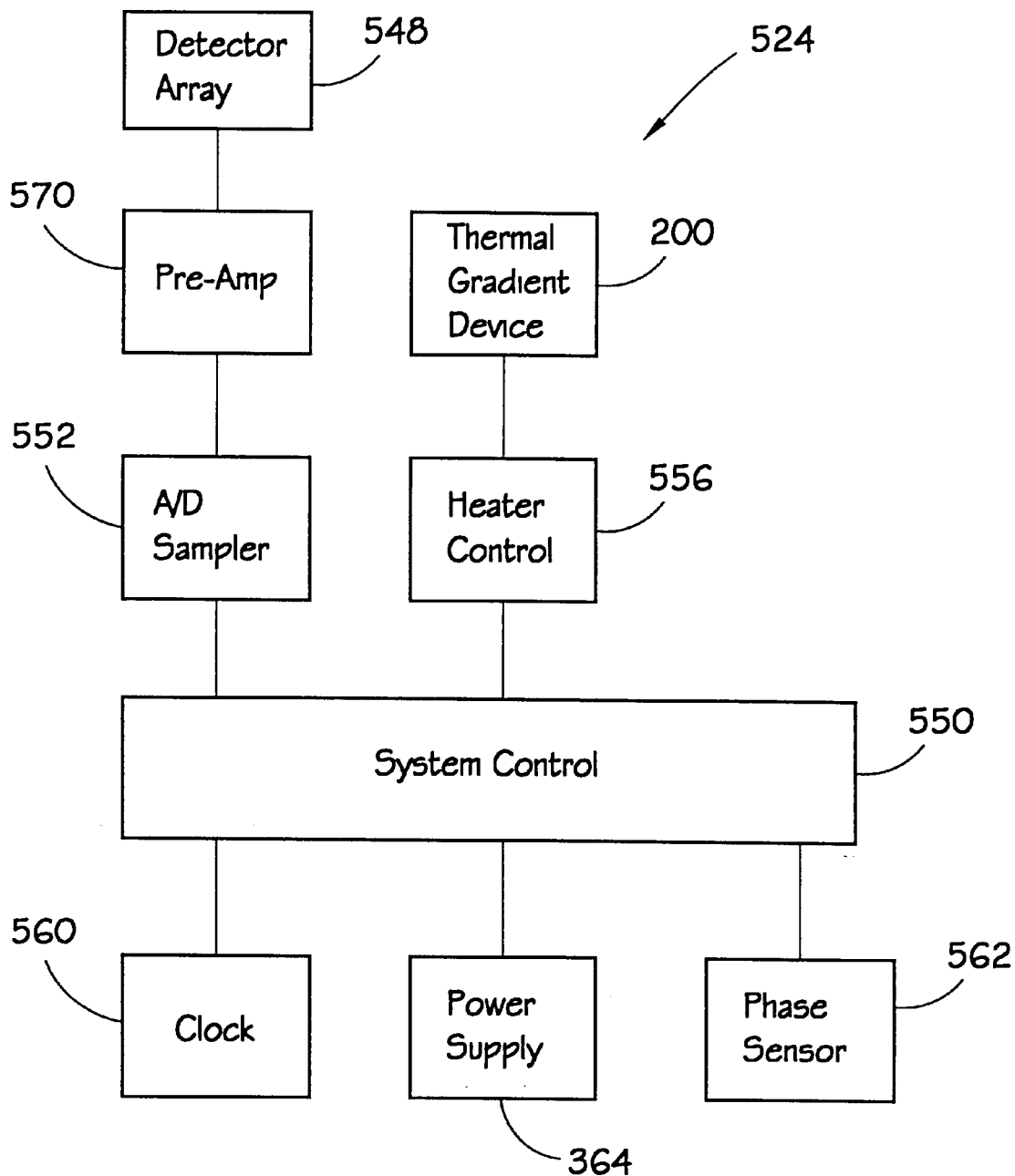
FIG. 6 is a schematic representation of the data capture and control electronics of the spectrometer shown in FIG. 5.

Referring now to FIG. 6, the data capture and control system 524 can be broken down into a number of functional elements, including an overall system control 550, an analog to digital (A/D) sampler 552, a heater control 556, a clock circuit 560 and an AC power line phase sensor 562.

The data capture and control system 524 receives power from a power supply 564, which in this embodiment of the invention is in the form of a battery, to improve isolation of the spectrometer 510 from AC power frequency interference.

The output signals from the detector array 548 are small, and are passed to a preamplifier 570. The preamplifier 570 boosts the magnitude of the signals before the signals are sampled by the A/D sampler 552. This sampling is done at an appropriate time as determined by the system control 550, and as discussed in more detail below.

Similarly, the system control 550 operates the heater control 556 at a prescribed frequency to intermittently switch power to the heater of thermal gradient device 200.

The system control 550 receives input from a clock circuit 560 for use in timing and synchronizing the various steps that take place in operation of the spectrometer 510.

The power line phase sensor 562 is used to sense the phase of AC power line interference. Output from the phase sensor 562 is used by the system control 550 as a trigger for various steps in the operation of the spectrometer 510, as described in more detail below. By synchronizing the operation of the spectrometer to the phase of power line interference in this way, the effect of such interference on the output of the spectrometer is reduced.

In use, the spectrometer 510 is powered up and an appropriate time interval is allowed to pass in order to allow the various subsystems to stabilize. In particular, the thermal mass window 200 should generally be permitted to reach its stable operating temperature.

During operation of the spectrometer 510, dry gas is continuously supplied to the interior of the housing 518 from the dry gas source 522. This ensures that substantially no moisture condenses on the output end of thermal mass device 200, which is generally at a temperature below the dew point of the air surrounding the spectrometer 510. This is important because the presence of water on the cold thermal mass window would interfere with the infrared emissions received by the spectrometer 510, causing inaccuracies in the data collected by the spectrometer.

After the spectrometer has reached a stable operating condition, a patient puts an arm or other body part over the window 208.

The contact between cold window 208, chilled by conductive heat loss to thermal mass window 200, and the skin of the patient transfers heat conductively from the patient's skin to thermal mass window 200. This generates a temperature differential between the skin and the interior of the patient, and over the course of the measurement cycle, this temperature differential propagates into the patient's arm in the form of a "cold wave". As the "cold wave" propagates into the patient's arm, the infrared emissions from the arm vary as described in at least one of the incorporated references.

The infrared emissions from the arm pass from the window 208 through the thermal mass window, through the infrared transmission path 542, and thence into the homogenizer 544.

In the homogenizer 544, the infrared emissions are scrambled or unfocused, so that all of the sensors in the infrared detector array 548 are equally affected by any non-uniformities in the infrared emissions. Non-uniformities may be created in the infrared emissions by, for example, a blemish on the patient's skin. By providing the homogenizer 544, each sensor in the detector array 548 receives an equal signal from all parts of the patient's skin.

Upon exiting the homogenizer 544, the infrared emissions pass through the respective single wavelength infrared filters positioned in front of each of the nine sensors in the infrared detector array 548. Accordingly, each sensor generates a signal which is proportional to the infrared energy at a characteristic wavelength, which is then passed to the preamplifier 570.

The preamplifier 570 amplifies the signals received from the sensors in the detector array. The signals are then passed to the A/D sampler 552.

The A/D sampler 552, which was activated by the system control 550, samples the signals received from the preamplifier 570 at between 1 and 20 ms intervals as the cold wave propagates into the patient's epidermal layer.

The initial actuation of A/D sampler 552 is synchronized to a particular phase of the surrounding power line interference by the system control 550, as sensed by the 60 Hz power line phase sensor 562. By synchronizing the commencement of the measurement cycle of the spectrometer in this manner, the effect of power line interference is felt substantially equally in every measurement cycle. Due to the comparative nature of the processing of the data gathered by the spectrometer, this synchronization technique improves the accuracy of the data captured by the spectrometer.

After a measurement A/D sampler 552 ceases sampling the signals received from the infrared detector array 548.

For the spectrometer illustrated in FIG. 6, the system control 550 is a Dell XPS personal computer which has an built-in clock 560, a monitor for the display of the captured data, a keyboard, and a disk drive for storing the captured data. The A/D sampler 552 is an Intelligent Instrumentation PCI system, the power supply is a battery pack from SRS, and the temperature control 556 is a CAL 3200.

As far as the remainder of the spectrometer 510 is concerned, dry gas source 522 is a supply of pure nitrogen.

The homogenizer is a 100 mm by 37 mm by 37 mm square tube with the inside walls plated with gold. The inside walls of the tube are highly polished and are therefore highly reflective to the infrared light passing through the homogenizer. The sensors in the infrared detector array are photovoltaic MCT infrared detectors supplied by Fermionics Inc.

After the measurement cycles have been completed by one of the spectrometers described herein, the data are processed as described in accordance with a subsurface thermal gradient spectrometric methodology. Such methodologies include, but are not necessarily limited to: U.S. Pat. No. 6,161,028; U.S. patent application Ser. No. 08/820,378; and U.S. patent application Ser. No. 08/816,723, each of which have been incorporated herein by reference.

It will be appreciated that many modifications can be made to the spectrometers described above without departing from the spirit and scope of the invention.

For example, the three by three detector array 548 may be replaced by a single infrared sensor behind a variable filter wheel. The filter wheel will then rotate to provide the desired bands of infrared light to the single infrared sensor. In such a case, it will not be necessary to provide a homogenizer to equalize the infrared light between a number of infrared detectors in an array.

Also, room temperature infrared sensors may be used instead of sensors requiring cryogenic cooling. In such a case, the dewar vessel 546 will of course not be required.

Further, it will also be appreciated that energy at more or less than nine infrared wavelengths may be sensed to provide more or less information on the infrared spectrum emitted from the tissue. Generally, there is a tradeoff here between cost and accuracy, with more sensors/wavelengths sensed providing a better tolerance of extraneous factors and a more accurate final output. In a low cost production version therefor, where less accuracy may be acceptable, fewer sensors may be used.

Similarly, in a production version of the spectrometer, it may not be necessary to provide a preamplifier to boost the output signals.

In use, it may be necessary in some circumstances to calibrate the spectrometer of the present invention in the field. While such calibration presents no particular difficulty in the laboratory environment, it will be appreciated that accurate calibration in the field presents some rather interesting challenges. Calibration of an instrument such as the type taught herein often requires the use of standards. In its simplest form a standard for calibrating a thermal gradient spectrometer optimized for determining glucose concentrations is nothing more than an aqueous solution of glucose, where the exact concentration of glucose is known. Use of such a simple standard presents at least two problems however.

First, once a standard solution leaves the laboratory it is subject to a wide variety of environmental effects which can serve to degrade its accuracy. Such effects include, but are not limited to evaporation, contamination, fermentation, dilution, sundry photochemical effects, spillage, and the like. Given the need for extremely precise measurements afforded by the principles of the present invention, any degradation in accuracy is unacceptable.

A second problem lies in the fact that a simple solution of glucose cannot properly mimic the physiology of human tissue. Tissue, and most importantly skin, is a layered structure. Accordingly, the principles of the present invention contemplate the use of layered polymeric standard structures which closely mimic human skin. A number of such standards, each containing a different concentration of glucose, may be used.

One structure for such a standard includes a number of polymeric layers. The first layer, that which is placed in contact with the optical window of the spectrometer of the present invention is intended to mimic the stratum corneum, and has the following properties:

Thickness=50 µm+/−20 µm;
Moisture content less than 20%;
No spectral features in the infrared band from 3–12 µm;
Known thermal impedance; and
Known thermal capacitance.

The second layer mimics the epidermis and has the following properties:

Thickness=300 µm+/−50 µm;
Moisture content=80%+/−10%;
Glucose spectral features at 9.6 µm;
No other spectral features in the infrared band from 3–12 µm;
Known thermal impedance; and
Known thermal capacitance.

Standards are provided at a variety of glucose concentrations. Useful concentrations might be:

0% glucose;
50 mg/dL glucose (physiological hypoglycemia);
100 mg/dL glucose (physiological normal);
500 mg/dL glucose (physiological hyperglycemia); and
1000 mg/dL glucose (outside the physiological limits).

The standards are packed in a hermetic container and treated to prolong shelf life and to retard microbial growth. Sterility may, or may not be desirable. The container, and the standards themselves should have imprinted thereon data about the standard including its glucose concentration. The labeling could be machine-readable, for example, using a bar code.

In use, the spectrometer could be placed in a calibration mode, manually or automatically upon presentation of the standard thereto. The spectrometer then reads the encoded information from the standard, or as manually entered. The spectrometer then scans the standard. When complete, the instrument may prompt for the next standard in the series. When all standards in the series have been scanned, the spectrometer post-processes the data:

The instrument may determine that it is within specification, and so notify the operator;

The instrument may determine that it is out of specification and may perform an automatic adjustment. It will then notify the operator that the adjustments have been successfully accomplished.

The instrument may determine that is out of specification and requires manual adjustment. The operator must be notified accordingly.

In each of the above cases, operator notification may additionally require a network connection to a computer or remote database. Such network connection may provide not only a repository for calibration information for a number of instruments, but may serve to automatically calibrate the instrument from the remote location. In similar fashion, the network connection may also be utilized to retain a remote database of patient information, and for a repository of treatment options given a certain patient history and reading.

The Applicants claim:

1. A solid-state thermal gradient device configured for measurement of analyte concentrations in heterogeneous material, the device comprising:
a calibration standard which mimics the physiology of human tissue and which contains an analyte at a known concentration;
an infrared transmissive thermal mass; and
an intermittent heating means in operative combination with the infrared transmissive thermal mass.

2. A device as in claim 1 wherein said calibration standard includes a machine readable calibration standard.

3. A device as in claim 2 wherein said machine readable calibration standard comprises a bar code.

4. A device configured for measurement of analyte concentrations in heterogeneous material, the device comprising:
a data transmission connection to at least one of a computer and a remote database, wherein said computer and remote database are configured for at least one of transmitting and receiving data from the group consisting of: calibration data; patient data; and treatment data;
an infrared transmissive window; and
an intermittent heating means in operative combination with the infrared transmissive window.

5. A method for forming a solid state thermal gradient device, the method comprising the steps of:
forming an infrared transmissive thermal mass comprising an infrared transmissive germanium cylinder;
forming an infrared transmissive heating layer on a surface of, and in operative combination with, the infrared transmissive thermal mass, wherein the infrared transmissive heating layer comprises an infrared transmissive wire-grid heating element; and
providing a means for intermittently energizing the infrared transmissive heating layer.

6. The method of claim 5 further comprising the steps of:
maintaining the infrared transmissive germanium cylinder within a specified temperature range disposing a heat exchanger means, in thermal combination with the infrared transmissive germanium cylinder; and
preventing condensation on at least one surface of the infrared transmissive germanium cylinder,
wherein the infrared transmissive germanium cylinder, the infrared transmissive thermal impedance layer, and the infrared transmissive wire-grid heating element form an optical pathway for the transmission of infrared energy therethrough.

7. A device configured for measuring analyte concentrations in heterogeneous material, the device comprising:
an infrared transmissive window having a temperature;
a heat exchanger capable of changing the temperature of the infrared transmissive window; and
an infrared transmissive thermal impedance layer disposed between, and in thermal contact with, the infrared transmissive window and the heat exchanger, such that an optical pathway configured for transmission of infrared electromagnetic radiation extends through the infrared transmissive window and the infrared transmissive thermal impedance layer.

8. The device of claim 7, wherein the infrared transmissive window is selected from the group consisting of: germanium, silicon and diamond.

9. The device of claim 7, wherein the heat exchanger is selected from the group consisting of: electrical resistance heating grid; thermo-electric heater; and wire bridge heating grid.

10. The device of claim 7, further comprising a network connection configured to provide analyte concentration information to at least one of a computer and a remote database.

11. A method for measuring analyte concentrations in a heterogeneous material, the method comprising:

positioning an infrared transmissive window in thermal communication with the heterogeneous material, the infrared transmissive window having a temperature;

periodically altering the temperature of the infrared transmissive window such that thermal energy is periodically supplied to or removed from the heterogeneous material;

receiving infrared radiation from the heterogeneous material through an optical pathway in the infrared transmissive window; and analyzing at least a portion of the received infrared radiation in a spectrometer for production of an analyte concentration datum for the heterogeneous material.

12. The method of claim 11, wherein the temperature of the infrared transmissive window is altered using a device from the group consisting of: heat exchanger, electrical resistance heating grid, thermo-electric heater and wire bridge heating grid.

13. The method of claim 11, wherein the heterogeneous material is a living tissue.

14. The method of claim 11, wherein the infrared transmissive window comprises a material selected from the group consisting of: germanium, diamond and silicon.

15. The method of claim 11, further comprising transmitting the analyte concentration datum to at least one of a computer and a remote database via a network connection.

* * * * *